(12) United States Patent
Ross

(10) Patent No.: US 9,877,766 B2
(45) Date of Patent: Jan. 30, 2018

(54) SPLIT HEXALOBE DRIVER DEVICE FOR USE IN SURGICAL PROCEDURES

(71) Applicant: Thomas Ross, Austin, TX (US)

(72) Inventor: Thomas Ross, Austin, TX (US)

(73) Assignee: Renovis Surgical Technologies, Inc., Redlands, CA (US)

( * ) Notice: Subject to any disclaimer, the term of this patent is extended or adjusted under 35 U.S.C. 154(b) by 347 days.

(21) Appl. No.: 14/822,082

(22) Filed: Aug. 10, 2015

(65) Prior Publication Data

US 2017/0042600 A1     Feb. 16, 2017

(51) Int. Cl.
  *A61B 17/58*   (2006.01)
  *A61B 17/60*   (2006.01)
  *A61F 2/00*    (2006.01)
  *A61B 17/88*   (2006.01)

(52) U.S. Cl.
  CPC .............................. *A61B 17/8888* (2013.01)

(58) Field of Classification Search
  CPC combination set(s) only.
  See application file for complete search history.

(56) References Cited

U.S. PATENT DOCUMENTS 3,831,648 A * 8/1974 Hill ................. B25B 15/005
                                            81/448

* cited by examiner

*Primary Examiner* — Sameh Boles
(74) *Attorney, Agent, or Firm* — Clements Bernard Walker PLLC; Christopher L. Bernard

(57) ABSTRACT

A driver device (hexalobe or otherwise) that includes a handle portion, an elongate shaft portion, and an end portion that includes a screw engagement portion and a split manufactured offset from the central axis of the end portion and/or the screw engagement portion, forming two asymmetric halves of the end portion and/or screw engagement portion. This screw engagement portion is slightly oversized relative to the corresponding tool engagement recess of the locking cap, set screw, or bone screw. Thus, when the screw engagement portion is pressed into the corresponding tool engagement recess of the locking cap, set screw, or bone screw, the split manufactured offset from the central axis of the end portion and/or the screw engagement portion allows the screw engagement portion to compress slightly, creating a friction fit between the screw engagement portion and the corresponding tool engagement recess of the locking cap, set screw, or bone screw.

7 Claims, 8 Drawing Sheets

SPLIT HEXALOBE DRIVER DEVICE FOR USE IN SURGICAL PROCEDURES

FIELD OF THE INVENTION

The present invention relates generally to a split hexalobe driver device for use in surgical procedures. More specifically, the present invention relates to a split hexalobe driver device that is used to retain and rotate locking caps, set screws, and bone screws used in orthopedic surgical procedures and the like.

BACKGROUND OF THE INVENTION

Various conventional split hexalobe driver devices exist for retaining and rotating locking caps, set screws, and bone screws used in orthopedic surgical procedures and the like. These driver devices typically include a handle portion, an elongate shaft portion, and an end portion that includes a screw engagement portion and a split manufactured down the central axis of the end portion and/or the screw engagement portion, forming two symmetric halves of the end portion and/or screw engagement portion. This screw engagement portion is slightly oversized relative to the corresponding tool engagement recess of the locking cap, set screw, or bone screw. Thus, when the screw engagement portion is pressed into the corresponding tool engagement recess of the locking cap, set screw, or bone screw, the split manufactured down the central axis of the end portion and/or the screw engagement portion allows the screw engagement portion to compress slightly, creating a friction fit between the screw engagement portion and the corresponding tool engagement recess of the locking cap, set screw, or bone screw. As a result, the locking cap, set screw, or bone screw is retained by the screw engagement portion prior to and while being rotated.

Because the split is manufactured down the central axis of the end portion and/or the screw engagement portion and two symmetric halves of the end portion and/or screw engagement portion are formed, when the driver device and locking cap, set screw, or bone screw are rotated, the two symmetric halves of the end portion and/or screw engagement portion do not have sufficient strength to resist the torque applied to them, the two symmetric halves of the end portion and/or screw engagement portion twist and/or otherwise deform slightly, and the driver device fails to effectively and/or adequately rotate the locking cap, set screw, or bone screw. Thus, what is still needed in the art is an improved driver device that avoids this problem.

BRIEF SUMMARY OF THE INVENTION

In various exemplary embodiments, the present invention provides a driver device (hexalobe or otherwise) that includes a handle portion, an elongate shaft portion, and an end portion that includes a screw engagement portion and a split manufactured offset from the central axis of the end portion and/or the screw engagement portion, forming two asymmetric halves of the end portion and/or screw engagement portion. This screw engagement portion is slightly oversized relative to the corresponding tool engagement recess of the locking cap, set screw, or bone screw. Thus, when the screw engagement portion is pressed into the corresponding tool engagement recess of the locking cap, set screw, or bone screw, the split manufactured offset from the central axis of the end portion and/or the screw engagement portion allows the screw engagement portion to compress slightly, creating a friction fit between the screw engagement portion and the corresponding tool engagement recess of the locking cap, set screw, or bone screw. As a result, the locking cap, set screw, or bone screw is retained by the screw engagement portion prior to and while being rotated.

However, because the split is manufactured offset from the central axis of the end portion and/or the screw engagement portion and two asymmetric halves of the end portion and/or screw engagement portion are formed, when the driver device and locking cap, set screw, or bone screw are rotated, the larger of the two asymmetric halves of the end portion and/or screw engagement portion has sufficient strength to resist the torque applied to it and the smaller of the two asymmetric halves of the end portion and/or screw engagement portion is not further loaded, the two asymmetric halves of the end portion and/or screw engagement portion do not twist or otherwise deform, and the driver device effectively and adequately rotates the locking cap, set screw, or bone screw.

In one exemplary embodiment, the present invention provides a surgical driver device, including: a handle portion; an elongate shaft portion coupled to the handle portion; and an end portion coupled to the elongate shaft portion; wherein the end portion includes a screw engagement portion defining a relief split manufactured along its length offset from a central axis of the screw engagement portion; and wherein the relief split forms two asymmetric halves of the screw engagement portion. Optionally, the elongate shaft portion includes more than one component. Optionally, the relief split extends into the end portion and is offset from a central axis of the end portion and forms two asymmetric halves of the end portion. Optionally, a first half of the two asymmetric halves of the screw engagement portion forms a portion of a substantially hexalobe pattern. Optionally, a second half of the two asymmetric halves of the screw engagement portion forms a substantially rectangular pattern. The first half of the two asymmetric halves of the screw engagement portion is substantially larger than the second half of the two asymmetric halves of the screw engagement portion. One of the two asymmetric halves of the screw engagement portion is configured to deflect into the relief split when the two asymmetric halves of the screw engagement portion are disposed in a corresponding tool engagement recess of a screw. One of the two asymmetric halves of the screw engagement portion has sufficient rigidity to resist rotation and/or deflection when the two asymmetric halves of the screw engagement portion are disposed in a corresponding tool engagement recess of a screw and the screw engagement portion of the surgical driver device and the screw are collectively rotated.

In another exemplary embodiment, the present invention provides a surgical driver method, including: providing a handle portion; providing an elongate shaft portion coupled to the handle portion; and providing an end portion coupled to the elongate shaft portion; wherein the end portion includes a screw engagement portion defining a relief split manufactured along its length offset from a central axis of the screw engagement portion; and wherein the relief split forms two asymmetric halves of the screw engagement portion. Optionally, the elongate shaft portion includes more than one component. Optionally, the relief split extends into the end portion and is offset from a central axis of the end portion and forms two asymmetric halves of the end portion. Optionally, a first half of the two asymmetric halves of the screw engagement portion forms a portion of a substantially hexalobe pattern. Optionally, a second half of the two asymmetric halves of the screw engagement portion forms a substantially rectangular pattern. The first half of the two asymmetric halves of the screw engagement portion is substantially larger than the second half of the two asymmetric halves of the screw engagement portion. One of the two asymmetric halves of the screw engagement portion is configured to deflect into the relief split when the two asymmetric halves of the screw engagement portion are disposed in a corresponding tool engagement recess of a screw. One of the two asymmetric halves of the screw engagement portion has sufficient rigidity to resist rotation and/or deflection when the two asymmetric halves of the screw engagement portion are disposed in a corresponding tool engagement recess of a screw and the screw engagement portion of the surgical driver device and the screw are collectively rotated.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Again, in various exemplary embodiments, the present invention provides a driver device (hexalobe or otherwise) that includes a handle portion, an elongate shaft portion, and an end portion that includes a screw engagement portion and a split manufactured offset from the central axis of the end portion and/or the screw engagement portion, forming two asymmetric halves of the end portion and/or screw engagement portion. This screw engagement portion is slightly oversized relative to the corresponding tool engagement recess of the locking cap, set screw, or bone screw. Thus, when the screw engagement portion is pressed into the corresponding tool engagement recess of the locking cap, set screw, or bone screw, the split manufactured offset from the central axis of the end portion and/or the screw engagement portion allows the screw engagement portion to compress slightly, creating a friction fit between the screw engagement portion and the corresponding tool engagement recess of the locking cap, set screw, or bone screw. As a result, the locking cap, set screw, or bone screw is retained by the screw engagement portion prior to and while being rotated.

However, because the split is manufactured offset from the central axis of the end portion and/or the screw engagement portion and two asymmetric halves of the end portion and/or screw engagement portion are formed, when the driver device and locking cap, set screw, or bone screw are rotated, the larger of the two asymmetric halves of the end portion and/or screw engagement portion has sufficient strength to resist the torque applied to it and the smaller of the two asymmetric halves of the end portion and/or screw engagement portion is not further loaded, the two asymmetric halves of the end portion and/or screw engagement portion do not twist or otherwise deform, and the driver device effectively and adequately rotates the locking cap, set screw, or bone screw.

Figure 1:
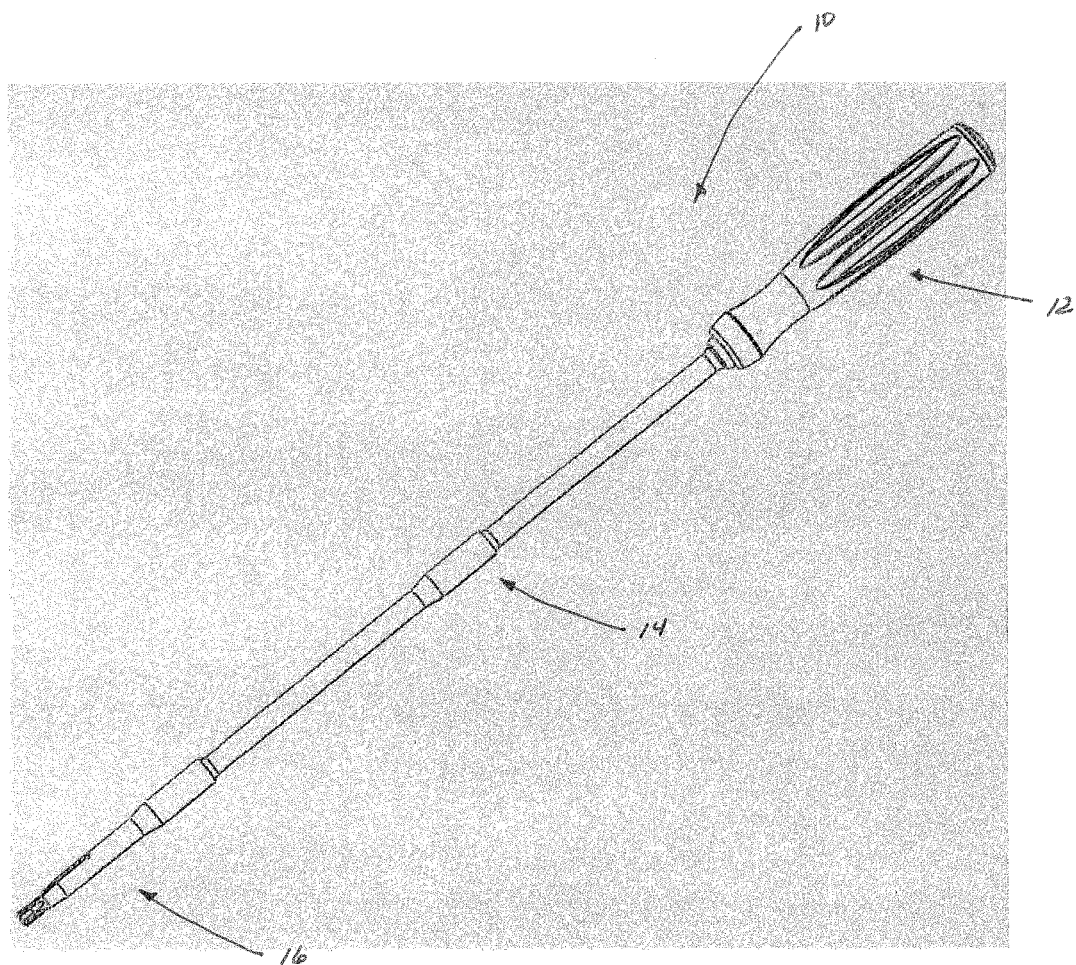
FIG. 1 is a perspective view of one exemplary embodiment of the driver device of the present invention.

Referring now specifically to FIG. 1, in one exemplary embodiment, the present invention provides a surgical driver device 10, including: a handle portion 12; an elongate shaft portion 14 coupled to the handle portion 12; and an end portion 16 coupled to the elongate shaft portion 14. The handle portion 12 may include any conventional or novel type of handle including a grip that allows a user to grasp, hold, and rotate the driver device 10, such that a screw can be advanced into and/or backed out of another structure. The handle portion 12 may also perform a ratcheting function. The handle portion 12 may be integrally formed with, welded to, threadingly engaged with, or otherwise fixedly or removably coupled to the elongate shaft portion 14, which may be a unitary structure or consist of several coupled components (as illustrated). Preferably, the handle portion 12 and the elongate shaft portion 14 share a common central axis, although this is not a requirement. Likewise, the elongate shaft portion 14 may be integrally formed with, welded to, threadingly engaged with, or otherwise fixedly or removably coupled to the end portion 16, which may also be a unitary structure (as illustrated) or consist of several coupled components. Preferably, the elongate shaft portion 14 and the end portion 16 also share a common central axis, although again this is not a requirement. All of these components may be made of a metal or other surgically compatible material.

Figure 2:
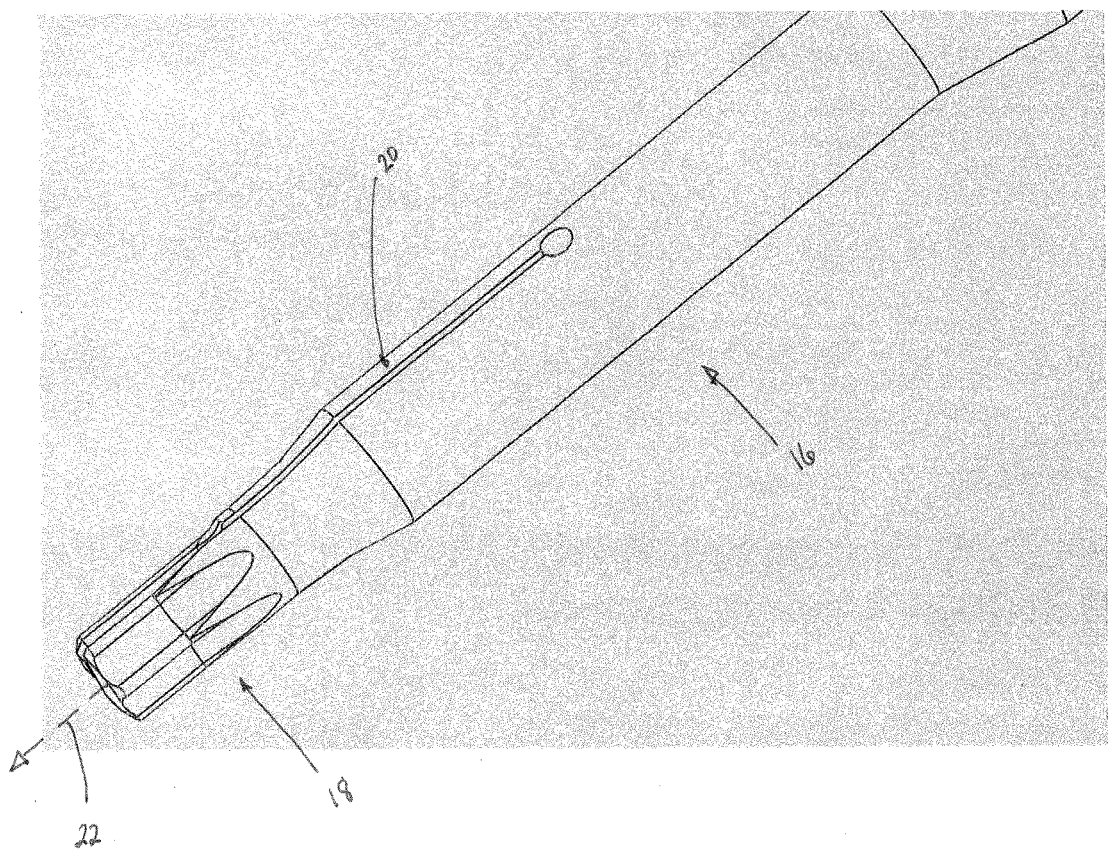
FIG. 2 is a partial perspective view of one exemplary embodiment of the driver device of the present invention, highlighting the end portion, screw engagement portion, and associated split and asymmetric halves thereof.
Figure 3:
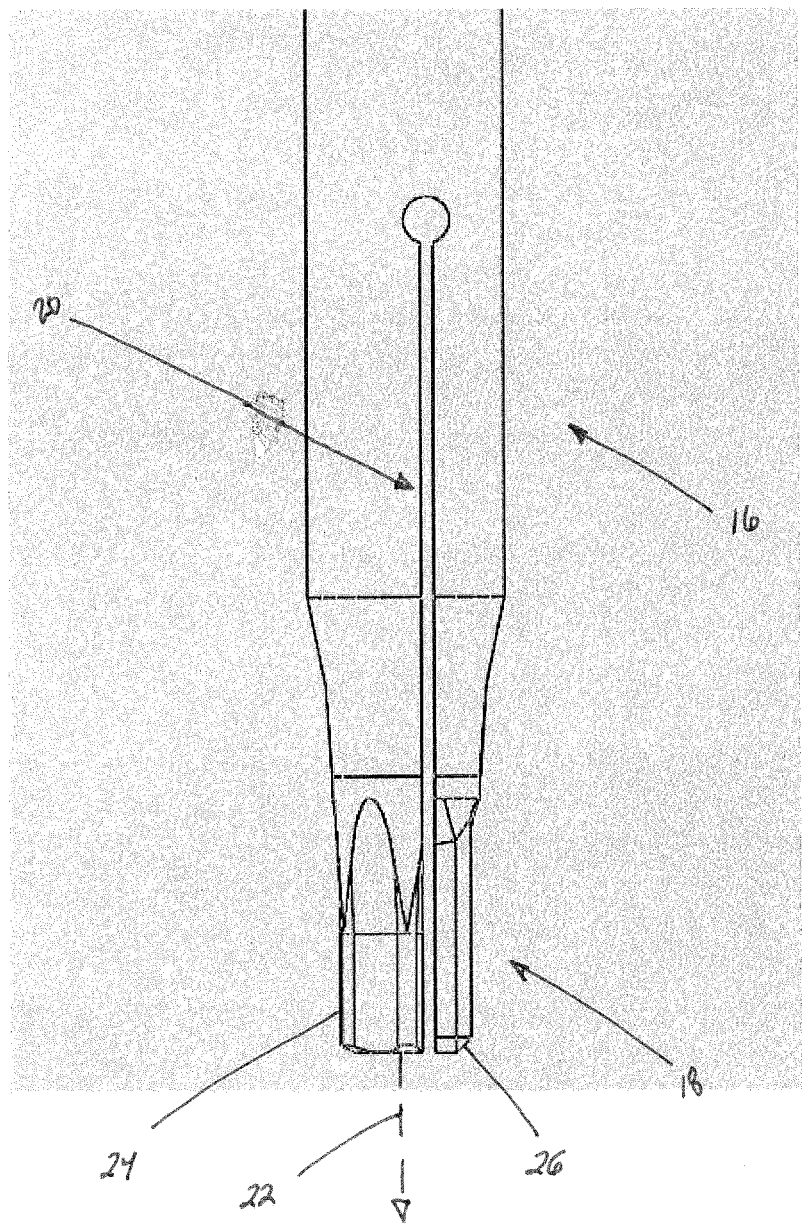
FIG. 3 is a partial planar view of one exemplary embodiment of the driver device of the present invention, again highlighting the end portion, screw engagement portion, and associated split and asymmetric halves thereof.
Figure 4:
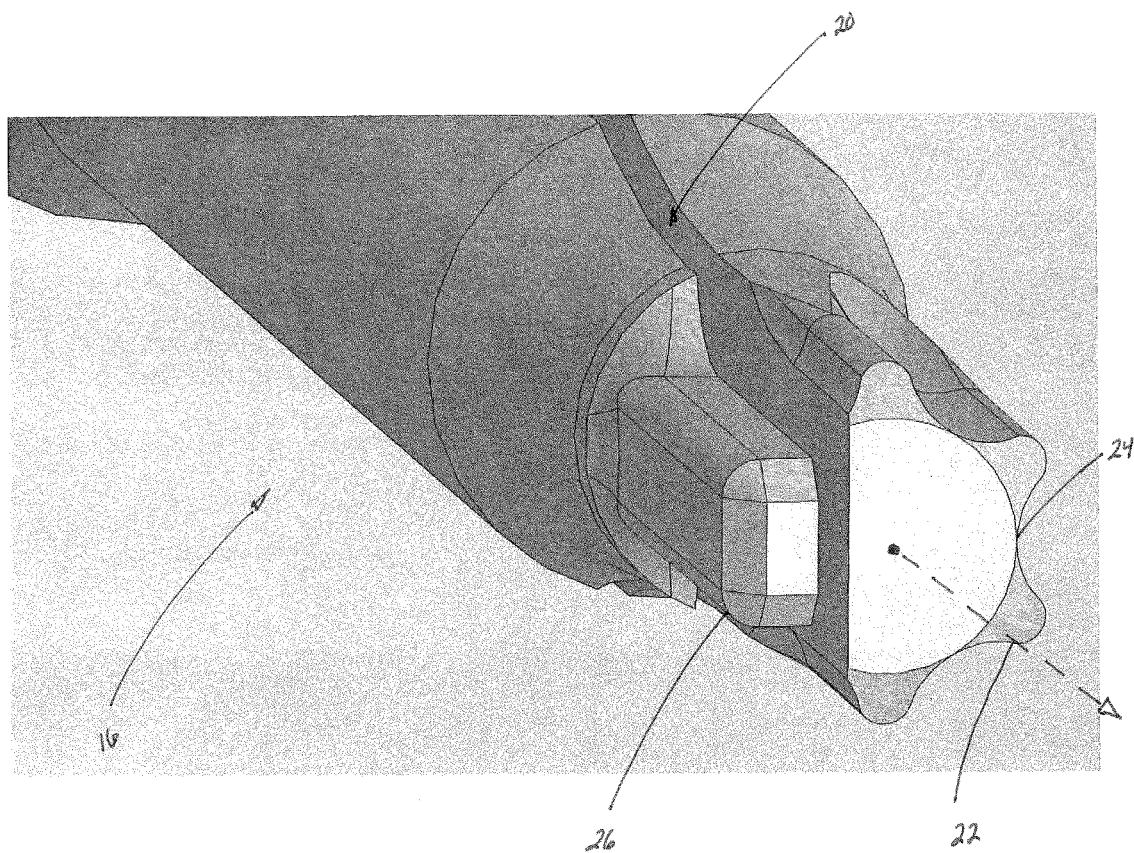
FIG. 4 is another partial perspective view of one exemplary embodiment of the driver device of the present invention, again highlighting the end portion, screw engagement portion, and associated split and asymmetric halves thereof.
Figure 5:
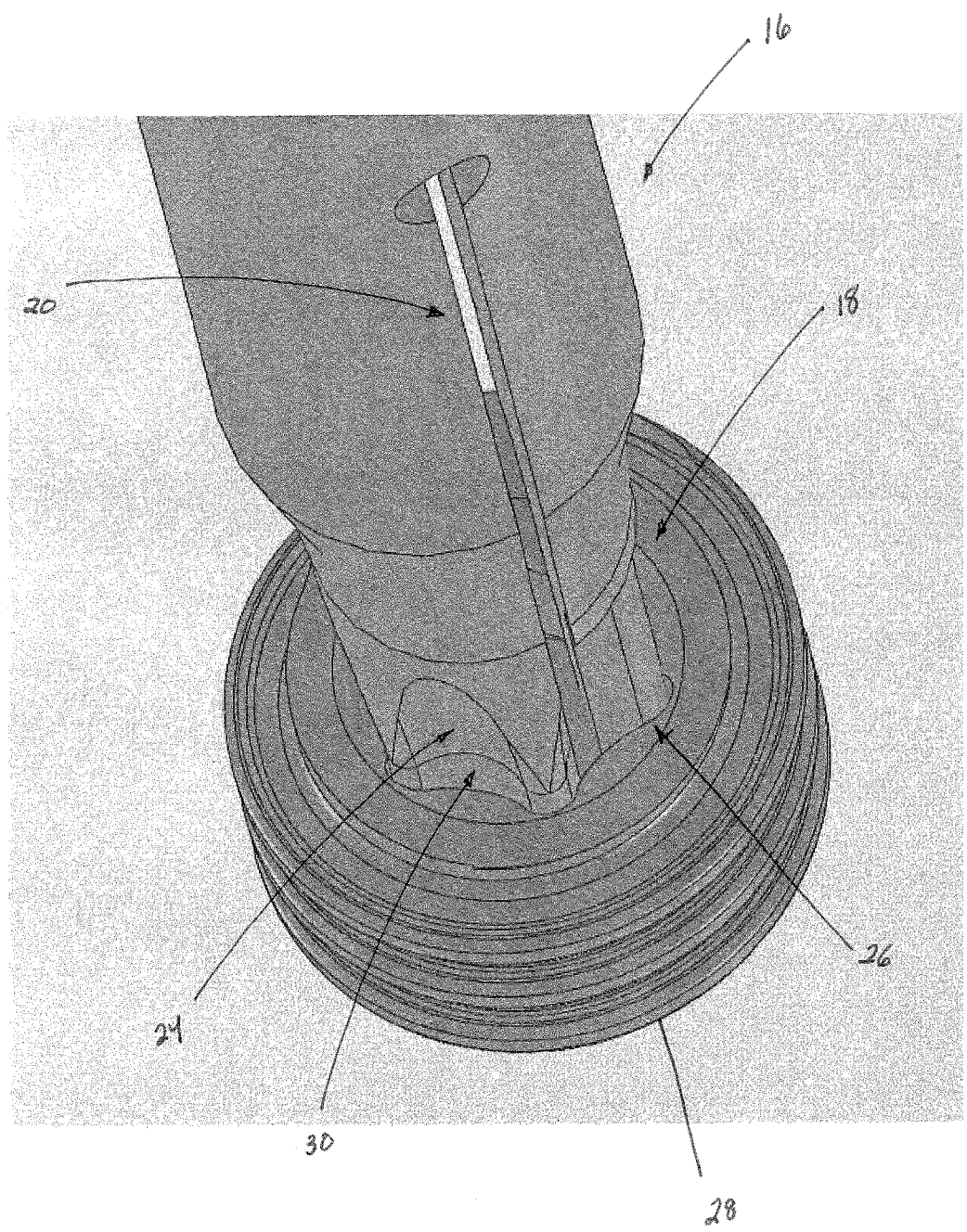
FIG. 5 is another partial perspective view of one exemplary embodiment of the driver device of the present invention, again highlighting the end portion, screw engagement portion, and associated split and asymmetric halves thereof, including the engagement of the screw engagement portion with a locking cap, set screw, or bone screw.
Figure 6:
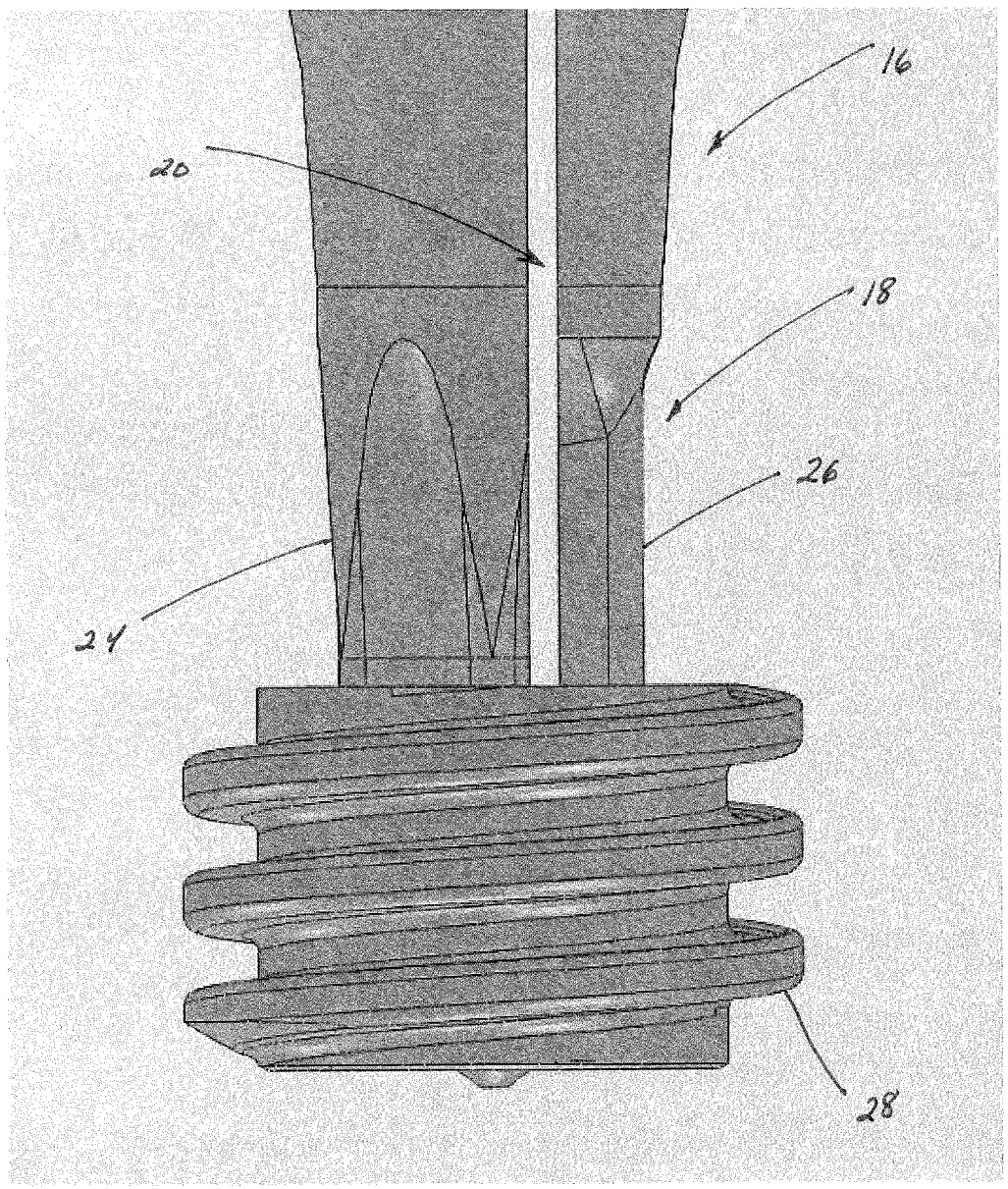
FIG. 6 is another partial planar view of one exemplary embodiment of the driver device of the present invention, again highlighting the end portion, screw engagement portion, and associated split and asymmetric halves thereof, including the engagement of the screw engagement portion with a locking cap, set screw, or bone screw.
Figure 7:
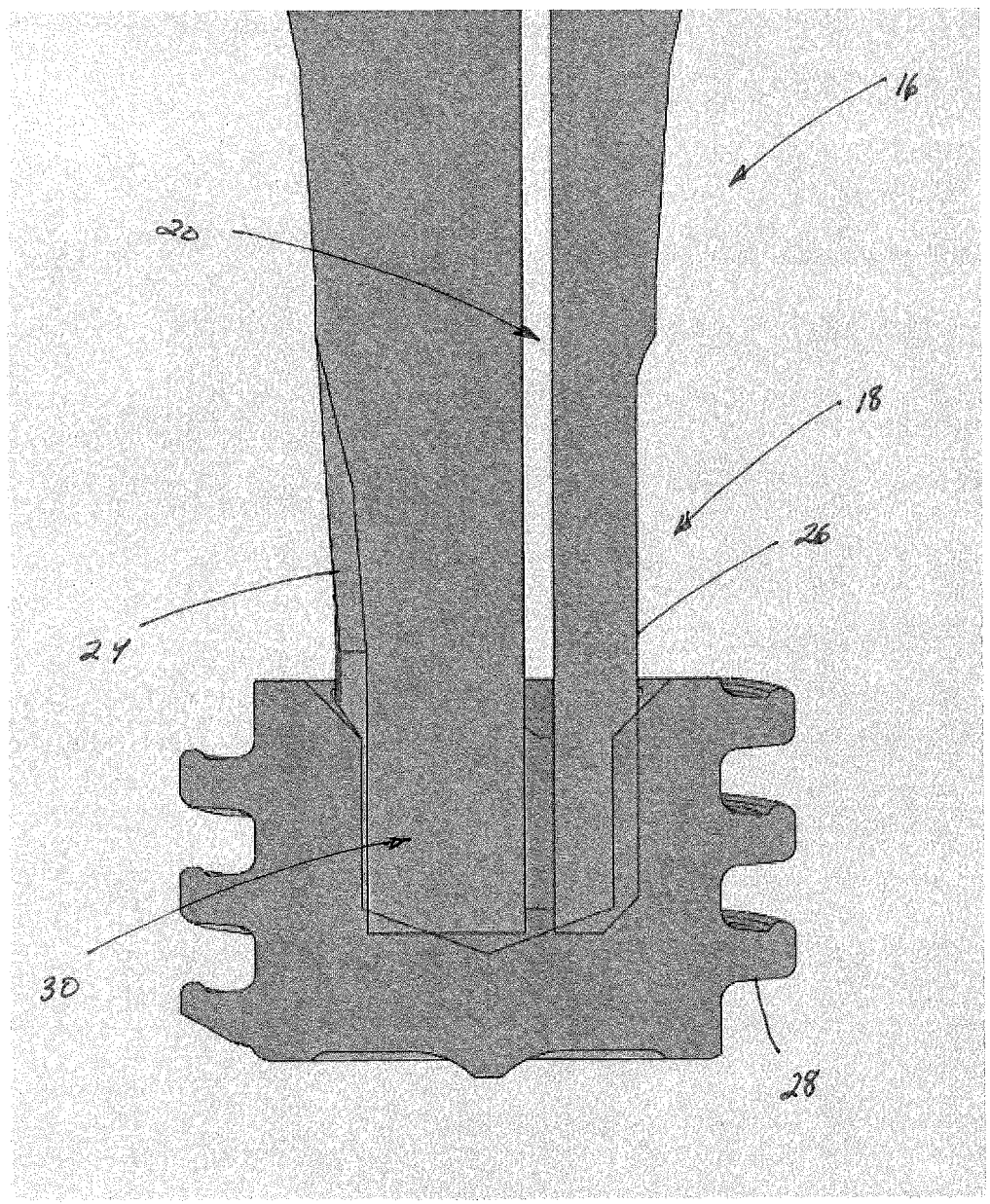
FIG. 7 is cross-sectional view of one exemplary embodiment of the driver device of the present invention, again highlighting the end portion, screw engagement portion, and associated split and asymmetric halves thereof, including the engagement of the screw engagement portion with a locking cap, set screw, or bone screw.
Figure 8:
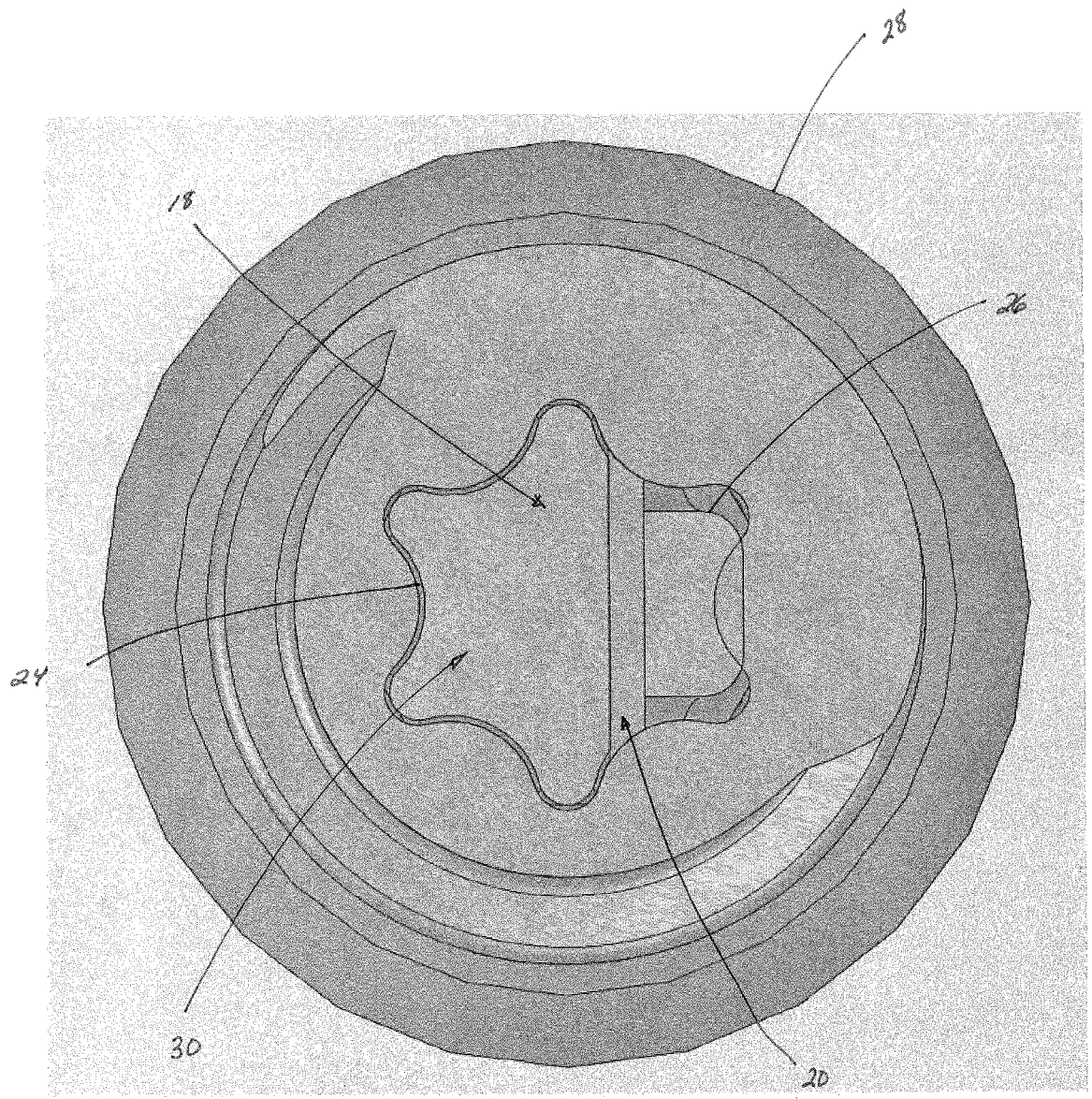
FIG. 8 is another partial planar view of one exemplary embodiment of the driver device of the present invention, again highlighting the end portion, screw engagement portion, and associated split and asymmetric halves thereof, including the engagement of the screw engagement portion with a locking cap, set screw, or bone screw.

Referring now specifically to FIGS. 2-4, in one exemplary embodiment, the end portion 16 includes a screw engagement portion 18 (optionally in conjunction with the remainder of the end portion 16) defining a relief split 20 manufactured along its length offset from a central axis 22 of the screw engagement portion 18. Thus, the relief split 20 forms two asymmetric halves 24 and 26 (FIGS. 3 and 4) of the screw engagement portion 18. A first (or driver) half 24 of the two asymmetric halves of the screw engagement portion 18 forms a portion of a substantially hexalobe or other screw pattern, suitable for engaging and driving a screw. A second (or spring) half 26 of the two asymmetric halves of the screw engagement portion 18 forms a substantially rectangular or other general pattern, suitable for engaging the screw, thereby creating a friction fit between the screw and the screw, the first half 24, and the second half 26, such that the screw is retained on the screw engagement portion 18 of the end portion 16 of the driver device 10 (FIG. 1). As can be seen, the first half 24 of the two asymmetric halves of the screw engagement portion 18 is substantially larger (in terms of diameter, volume, and/or length) than the second half 26 of the two asymmetric halves of the screw engagement portion 18. It should be noted that all edges of the end portion 16, the screw engagement portion 18, the first half 24 of the two asymmetric halves of the screw engagement portion 18, and the second half 26 of the two asymmetric halves of the screw engagement portion 18 may be chamfered or otherwise rounded, as appropriate, to promote safety and aide in engagement with the screw.

Referring now specifically to FIGS. 5-8, in one exemplary embodiment, the second 26 of the two asymmetric halves of the screw engagement portion 18 is configured to deflect into the relief split 20 when the two asymmetric halves 24 and 26 of the screw engagement portion 18 are disposed in a corresponding tool engagement recess 30 (FIGS. 5, 7, and 8) of a screw 28. The first 24 of the two asymmetric halves of the screw engagement portion 18 has sufficient rigidity to resist rotation and/or deflection when the two asymmetric halves 24 and 26 of the screw engagement portion 18 are disposed in the corresponding tool engagement recess 30 of the screw 28 and the screw engagement portion 18 of the driver device 10 (FIG. 1) and the screw 28 are collectively rotated.

Although a hexalobe driver device is illustrated and described herein, it will be readily apparent to those of ordinary skill in the art that the driver device and corresponding screw may utilize any suitable driver pattern, conventional or novel. Similarly, although a locking cap, set screw, or bone screw is illustrated and described herein, it will be readily apparent to those of ordinary skill in the art that the driver device of the present invention may be used with any type of screw, with the caveat that the present invention is primarily concerned with surgical screws. Accordingly, any/all of the components of the driver device are manufactured from a surgically compatible material and are sized/shaped in a conventional manner, depending on the specific surgical application.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A surgical driver device, comprising:
a handle portion;
an elongate shaft portion coupled to the handle portion; and
an end portion coupled to the elongate shaft portion;
wherein the end portion comprises a screw engagement portion comprising a relief split manufactured along its length offset from a central axis of the screw engagement portion; wherein the relief split forms two asymmetric halves of the screw engagement portion; and wherein a first half of the two asymmetric halves of the screw engagement portion forms a portion of a substantially hexalobe pattern comprising a plurality of circumferential curved recesses.

2. The surgical driver device of claim 1, wherein the elongate shaft portion comprises more than one component.

3. The surgical driver device of claim 1, wherein the relief split extends into the end portion and is offset from a central axis of the end portion and forms two asymmetric halves of the end portion.

4. The surgical driver device of claim 1, wherein a second half of the two asymmetric halves of the screw engagement portion forms a substantially rectangular pattern.

5. The surgical driver device of claim 4, wherein the first half of the two asymmetric halves of the screw engagement portion is substantially larger than the second half of the two asymmetric halves of the screw engagement portion.

6. The surgical driver device of claim 1, wherein one of the two asymmetric halves of the screw engagement portion is configured to deflect into the relief split when the two asymmetric halves of the screw engagement portion are disposed in a corresponding tool engagement recess of a screw.

7. The surgical driver device of claim 1, wherein one of the two asymmetric halves of the screw engagement portion has sufficient rigidity to resist rotation and/or deflection when the two asymmetric halves of the screw engagement portion are disposed in a corresponding tool engagement recess of a screw and the screw engagement portion of the surgical driver device and the screw are collectively rotated.

* * * * *